(12) United States Patent
Clarke et al.

(10) Patent No.: US 8,017,015 B2
(45) Date of Patent: Sep. 13, 2011

(54) MONOLITHIC COLUMN CHROMATOGRAPHY

(75) Inventors: Nigel Clarke, Oceanside, CA (US); Mildred M. Goldman, Laguna Niguel, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 1206 days.

(21) Appl. No.: 11/584,354

(22) Filed: Oct. 20, 2006

(65) Prior Publication Data

US 2008/0093300 A1 Apr. 24, 2008

(51) Int. Cl.
*B01D 15/08* (2006.01)

(52) U.S. Cl. .............. 210/635; 210/656; 210/198.2; 210/502.1

(58) Field of Classification Search ............... 210/656, 210/635, 198.2, 502.1
See application file for complete search history.

(56) References Cited

U.S. PATENT DOCUMENTS

| | | | |
|---|---|---|---|
| 5,624,875 | A | 4/1997 | Nakanishi et al. |
| 5,772,874 | A | 6/1998 | Quinn et al. |
| 5,795,469 | A | 8/1998 | Quinn et al. |
| 5,919,368 | A | 7/1999 | Quinn et al. |
| 5,968,367 | A | 10/1999 | Quinn et al. |
| 6,074,555 | A | 6/2000 | Boos et al. |
| 6,107,623 | A | 8/2000 | Bateman et al. |
| 6,110,362 | A | 8/2000 | Quinn et al. |
| 6,124,137 | A | 9/2000 | Hutchens et al. |
| 6,149,816 | A | 11/2000 | Quinn et al. |
| 6,156,273 | A * | 12/2000 | Regnier et al. .............. 422/70 |
| 6,204,500 | B1 | 3/2001 | Whitehouse et al. |
| 6,268,144 | B1 | 7/2001 | Koster |
| 6,398,962 | B1 | 6/2002 | Cabrera et al. |
| 6,531,060 | B1 | 3/2003 | Nakanishi et al. |
| 6,635,173 | B2 | 10/2003 | Brann et al. |
| 6,808,635 | B2 | 10/2004 | Brann et al. |
| 2004/0002081 | A1 | 1/2004 | Urthaler et al. |
| 2004/0099605 | A1 * | 5/2004 | Chiang et al. ............. 210/657 |
| 2004/0144715 | A1 * | 7/2004 | Kanehara et al. ........ 210/502.1 |

OTHER PUBLICATIONS

Alpert, A.J., "Hydrophilic-Interaction Chromatography for the Separation of Peptides, Nucleic Acids and Other Polar Compounds", Journal of Chromatography, 499:177-196 (1990).
Cabrera, K. et al., SilicaROD™—A new challenge in fast high-performance liquid chromatography separations, Trends Anal. Chem. 17:50 (1998).
Dorsey, J.G. et al., Liquid Chromatography: Theory and Methodology, Anal. Chem. 62:324 R (1990).
Fujita, T. et al., Chromatography in Presence of High Concentrations of Salts on Columns of Celluloses with and without Ion Exchange Groups (Hydrogen Bond Chromatography) Its Application to Purification of Yeast Enzymes, J. Biochem. (Tokyo), 87 (1):89 (1980).
Hjerten, S. et al., High-performance liquid chromatography on continuous polymer beds, J Chromatography 473:273 (1989).
Liao, J. et al., Continuous beds for standard and micro high-performance liquid chromatography, J Chromatography 586:21 (1991).

(Continued)

*Primary Examiner* — Ernest G Therkorn
(74) *Attorney, Agent, or Firm* — Foley & Lardner LLP

(57) ABSTRACT

Provided herein are methods of liquid column chromatography in which preparative chromatography is performed in-line with analytical chromatography. In particular aspects a monolithic preparative column is used to purify an analyte of interest from a mixture of other substances by applying the mixture to the column, reversing the flow through the column to elute the analyte, which is applied to an analytical column provided in-line with the preparative column. In other aspects, a single monolithic column is used to perform both the preparative chromatography and analytical chromatography steps in succession. In another aspect, a chromatography system is provided to perform preparative and analytical chromatography using a single monolithic column.

11 Claims, 10 Drawing Sheets

OTHER PUBLICATIONS

Merchant, M. and Weinberger, S.R., Recent advancements in surface-enhancer laser desorption/ionization-time of flight-mass spectrometry, *Electrophoresis* 21:1164-67 (2000).

Nakanishi, K. et al., Phase Separation in Gelling Silica-Organic Polymer Solution: Systems Containing Poly(sodium styrenesulfonate), J Am Ceram Soc 74:2518 (1991).

Tennikova, T.B. and Svec, F., High-performance membrane chromatography: highly efficient separation method for proteins in ion-exchange, hydrophobic interaction and reversed-phase modes, J Chromatogr 646:279 (1993).

Wright, G.L. et al., Proteinchip® surface enhanced laser desorption/ionization (SELDI) mass spectrometry: a novel protein biochip technology for detection of prostate cancer biomarkers in complex protein mixtures, *Prostate Cancer and Prostatic Diseases* 2:264-76 (1999).

Zimmer, D. et al., Comparison of turbulent-flow chromatography with automated solid-phase extraction in 96-well plates and liquid-liquid extraction used as plasma sample preparation techniques for liquid chromatography-tandem mass spectrometry, *J. Chromatogr. A* 854: 23-35 (1999).

\* cited by examiner

MONOLITHIC COLUMN CHROMATOGRAPHY

FIELD OF THE INVENTION

The present invention relates generally to the field of liquid column chromatography.

BACKGROUND OF THE INVENTION

Analytical liquid chromatography (e.g., high performance liquid chromatography or HPLC) is commonly used in the detection and quantitation of low molecular weight substances in biological samples and body fluid samples (e.g., blood, serum, or plasma). Such samples contain proteins and proteinaceous molecules, which can accumulate on many types of HPLC columns, thereby causing irreversible damage to such columns. For this reason, it is desirable to remove the proteins and other large molecular weight species prior to analysis of the sample for the analyte of interest. Methods of removal of proteins include precipitation, membrane filtration, and liquid-liquid or liquid-solid phase extraction.

An alternate method of removing proteins from a sample is preparative liquid chromatography. In order to adapt such a method to high throughput assays, high flow rates, short elution times, and moderate operating pressures are desirable. Accordingly, porous support materials for use in column chromatography which, simultaneously offer a selective retention of low molecular weight analytes (molecular weight<5000 Dalton), and make possible quantitative separation of proteins and other macromolecular components in a directly injected sample have recently been developed. One example of a column comprising such a porous support is a new column for use in HPLC, known as a monolithic column. Monolithic columns, in contrast to traditional HPLC columns that comprise packed particles, contain a single, solid compound as the stationary phase. This stationary phase is usually made up of a network of polymethacrylate or polystyrene copolymers, or bonded silica forming pores of varying size. Thus, in monolithic columns the mobile phase must flow through the pores of the solid stationary phase. Molecules within the mobile phase are then retained to a greater or lesser extent within the pores of the stationary phase (small molecules diffuse into the pores and are retained while large molecules are excluded from the pores and are not retained). Retention of small molecules may be further enhanced by binding to specific compounds incorporated into the interior of the pores.

SUMMARY OF THE INVENTION

Provided herein are methods of performing preparative liquid chromatography, using a monolithic column, in-line with analytical liquid chromatography. In such methods, an analyte or analytes of interest are separated from other substances in a complex mixture using a monolithic column under conditions whereby the analyte is retained on the column. The analyte is then eluted and supplied to an in-line analytical column for further separation and detection. Such methods offer the advantage of utilizing a monolithic column in the preparative chromatography, which allows for higher flow rates at moderate operating pressures, resulting in quick separations. The further combining of preparative chromatography in-line with analytical chromatography decreases the amount of handling by the operator which results in a fast, efficient, and inexpensive method amenable to high-throughput assays.

In one aspect of the invention, there are provided chromatographic methods for detecting one or more analytes in a sample containing a mixture of other substances. Such methods comprise: a) separating the one or more analytes from the other substances in a mixture using a first chromatography column comprising a monolithic sorbent having macropores and mesopores, using a first mobile phase under conditions such that the one or more analytes are retained on the first column and other substances are removed, b) eluting the one or more retained analytes by applying a second mobile phase to the column, c) directing the eluted one or more analytes to a second chromatography column in-line with the first column for further separation, and d) detecting the one or more analytes following the separation in step c).

In some embodiments the second mobile phase is applied to the column in the same direction as the flow in step a). In other embodiments, the second mobile phase is applied to the column in the opposite direction of the flow in step a).

In some embodiments, a monolithic column is used to separate small molecular weight analytes of interest from a mixture of large molecular weight species. Thus, a sample is loaded onto a monolithic column, comprising macropores and mesopores under conditions such that small molecule analytes are retained, while larger molecules are excluded and washed from the column with the eluent. After the large molecular weight species have been removed, the small molecule analyte is eluted from the column with a reverse flow of mobile phase and supplied directly to an in-line analytical column for further separation and analysis.

The above method can be applied to obtain preparative samples of small molecular weight analyte from various types of body fluids and using monolithic columns with various physical characteristics.

In another aspect of the invention, there are provided methods for achieving multiple chromatographic separations of one or more analytes from other substances in a sample using a single column. Such methods comprise: a) achieving a first chromatographic separation of one or more analytes from other substances, the separation occurring by applying the sample to a chromatography column comprising a monolithic sorbent having macropores and mesopores, using a first mobile phase under conditions such that the one or more analytes in the sample are retained on the column and other substances are removed, b) eluting the one or more retained analytes by applying a second mobile phase to the column in the opposite direction of the flow in step a), c) applying the eluted one or more analytes to the column under conditions whereby a second chromatographic separation is achieved. Such methods allow for the use of fewer columns and fewer HPLC pumps, resulting in a reduction in cost as well as savings in space. In addition, use of the column for analytical separation allows for enhanced recovery of analyte that may have remained adsorbed to the column during the first chromatographic separation.

In some embodiments of the above aspect of the invention, the first chromatographic separation is a preparative chromatographic separation and the second chromatographic separation is an analytical separation. In this method, a mixture containing small molecule analytes and larger molecules is applied to the monolithic column under conditions such that the small molecule analytes are retained on the column, whereas the large molecules pass through the column. One or more analytes of interest are then eluted using a reverse flow of a small volume of an organic solvent and recovered into a precolumn reservoir. The eluted one or more analytes are then resupplied to the monolithic column, and the system run under conditions sufficient for chromatographic separation and detection of the analyte or analytes of interest.

In certain embodiments of the above aspect of the invention, step c) further comprises retaining the one or more analytes on the column and eluting the one or more analytes using reverse flow. The eluted analytes may then be reapplied to the column under conditions whereby a third chromatographic separation is achieved.

In other embodiments of the above aspect of the invention, step c) further comprises running the one or more analytes through the column and monitoring the effluent for the one or more analytes. Monitoring may be performed by any of a number of instruments or detectors well-known to those of skill in the art. For example, analytes may be detected using mass spectrometers, UV/Vis absorbance detectors, photodiodearray detectors, fluorescence detectors, refractive index detectors, conductivity detectors, and the like.

In still other embodiments of the above aspect of the invention, step c) further comprises collecting the one or more analytes into fractions following the second (or third, etc.) chromatographic separation. Such fractions may be subjected to further analysis by chromatographic methods or other standard analytical methods.

The above methods can be applied to obtain preparative samples of small molecular weight analyte from various types of body fluids and using monolithic columns with various physical characteristics.

In another aspect of the invention, there is provided a chromatography system for achieving multiple chromatographic separations of one or more analytes from other substances in a sample using a single monolithic column. Such a system comprises as a central feature a multiport valve and a column comprising a continuous monolithic sorbent having interconnected macropores and mesopores. The system further includes a mobile phase supply, a sample injector, a reservoir, a detector, and a waste line. The system is configured as follows: the mobile phase supply connected to the sample injector, which is connected to one port of the multiport valve having individual ports. Each port of the multiport valve is further connected to one of the following: a reservoir (having a first end and a second end and wherein the reservoir is adapted to hold eluted analyte) wherein the first end of the reservoir is in fluid communication with a port of the valve and the second end of the reservoir is in fluid communication with a first opening of a column; a second opening of the column; a detector; and a waste line. The multiport valve is switchable between a first position and a second position. In the first position of the valve, the mobile phase supply (via the sample injector) is connected to the valve which is connected to the sample loop which is connected to the first opening of the column. The second opening of the column is connected to the valve which is further connected to the detector. In the second position of the valve, the orientation of the column with respect to the system is reversed so that the mobile phase supply is connected, via the valve to the second opening of the column. The first opening of the column is connected to the sample loop which is connected to the valve which is connected to the waste line.

The two operating positions of the multiport valve determine the direction of flow of mobile phase through the column. In the first position, fluid from the mobile phase supply travels via the sample injector to the valve which directs the flow through the reservoir, and into the first end of the column. Flow exits the column via the second opening of the column and enters the valve and is directed to a detector. When the valve is in the second position, the mobile phase enters the column through the second opening of the column and exits via the second opening, thus providing a flow of mobile phase through the column in the opposite direction as the flow of mobile phase when the valve is in the first position. Exiting mobile phase is further directed to a waste line.

In a particular embodiment of the above aspect of the invention, the system further comprises a second multiport valve. In this system the two valves are connected in tandem. Each port of the first multiport valve is connected to one of the following: a sample injector; a reservoir, having a first end and a second end and wherein the reservoir is adapted to hold eluted analyte, wherein the first end is in fluid communication with a port of the first multiport valve and the second end is in fluid communication with a first opening of a column, a second opening of the column; and a second multiport valve. The second multiport valve is further connected to one or more detectors and a waste line. The first multiport valve is switchable between a first position and a second position so that the valve controls the direction of the flow of mobile phase through the column. The second multiport valve is switchable between a first position and a second position so that the valve controls the flow of effluent to the detector or the waste line. Thus, the user of the system can change the orientation of the column with respect to the system (i.e., reverse the flow of solvent through the column) using the first valve. Further, the user can determine whether a particular detector or a waste line is in-line using the second valve.

In such a system, a sample is applied to the column using the solvent delivery system and the sample injector under conditions whereby small molecules are retained on the column while large molecular weight species flow through the column and are not retained. The solvent and large molecular weight species may be conducted to a waste line or to an in-line detector to monitor removal of the large molecules. Once the large molecular weight species have been washed from the column, flow of solvent through the column is reversed and the analyte is eluted from the column into the reservoir. Flow is reversed again and the analyte is reapplied to the column for further analytical separation. Following the analytical separation, the eluted analyte may be conducted to any of the one or more in-line detectors.

"Monolithic column" as used herein comprises a material (e.g., silica, glass, glass-ceramic, or polymeric components) having interconnected continuous macropores with a median diameter larger than 0.1 µm. A monolithic column also may additionally contain mesopores in the walls of the macropores. Mesopores preferably have a median diameter between 2 and 100 nm.

The interconnected macropores in the porous materials of a monolithic column may exhibit median diameters ranging from 0.1 to 50 µm; a preferred range for the median diameters of the macropores is from 0.2 to 20 µm or 0.2 to 10 µm.

Mesopores present in the walls of the macropores exhibit median diameters ranging from 2 to 100 nm; a preferred range for the median diameters of the mesopores is from 2 to 50 nm, and especially a range from 5 to 30 nm being preferred.

"Phenyl," "C-2," "C-8," and "C-18" as used herein refer to functional groups present on a column packing material. For example, a phenyl column exposes the material flowing through the column to unsubstituted phenyl groups, while a C-18 column exposes the material flowing through the column to unsubstituted straight or branched chain 18-carbon alkyl groups.

In some embodiments, the inner surface of the macro or mesopore is chemically modified. In particular aspects, the interior of the mesopores of a monolithic column are coated with a C4, C8, C18, or phenyl material to assist in the retention of hydrophobic analytes.

"Liquid chromatography" (LC) as used herein means a process of selective retention or retardation of one or more components of a fluid solution as the fluid flows through a column containing stationary material(s) made of a finely divided substance and/or a material having capillary passageways. Retention results from the relative partitioning of the components of the mixture between the stationery phase and the bulk fluid phase (i.e., mobile phase), the later of which moves through the stationery materials. LC is used for analysis and separation of mixtures of two or more substances. LC includes, for example, high turbulence liquid chromatography (HTLC), preparative chromatography, and analytical chromatography (e.g., HPLC).

"High turbulence liquid chromatography" (HTLC) as used herein refers to the use of turbulent flow to enhance the rate of mass transfer during column chromatography, improving the separation characteristics provided. This is in contrast to traditional HPLC analysis which relies on column packings in which laminar flow of the sample through the column is the basis for separation of the analyte of interest from the test sample. HTLC has been applied for sample preparation to detect drugs prior to analysis by mass spectrometry. See, e.g., Zimmer et al., *J. Chromatogr. A* 854: 23-35 (1999); see also, U.S. Pat. Nos. 5,968,367; 5,919,368; 5,795,469; and 5,772,874.

"Preparative chromatography" as used herein refers to coarse separation of a particular analyte from a mixture containing other substances that are grossly different from the analyte (e.g., a small molecule analyte may be separated from a mixture containing proteins and other large molecular weight species). Such methods involve the selective retention of a particular solute or analyte in a complex mixture by a column, while other components are not retained. The analyte is then selectively removed from the column and may be collected for further use or analysis. Typically, preparative chromatographic separations are followed by a finer separation, which allows for the separation of closely related molecules (i.e., analytical chromatography). Preparative chromatography does not necessarily involve large samples, or large columns (although very large columns are often used in preparative chromatography). In preparative chromatography, column diameters can range from a few millimeters to a meter or more, and mobile phase volumes may range from a few milliliters to hundreds of liters. In preparative chromatography, analytes eluted from the column may be collected in an in-line reservoir (e.g., sample loop or tubing). Alternatively, analytes, following elution from the preparative column, may be directed to an in-line analytical column for further analysis.

"Analytical chromatography" as used herein refers to a fine separation of closely related molecules (e.g., molecules of similar molecular weights). In analytical chromatography, analytes separated on a column, eluted from the column, and monitored or detected. The term "analytical column" as used herein refers to a chromatography column having sufficient chromatographic plates to effect a separation of an analyte from other materials in a sample, wherein such a separation is sufficient to allow detection and determination of the presence or amount of the analyte.

In methods provided herein a single monolithic column is used for both preparative chromatography and analytical chromatography. This is accomplished by changing the conditions under which each separation is performed. Such conditions include flow rate, composition of the mobile phase, and the direction of flow of mobile phase through the column.

"Separating" as used herein, refers to the process characterized by the spatial separation of the components of a mixture based on their partitioning differential between phases (i.e., mobile and stationary phases) in relative motion. Separating results from loading the sample onto the column and washing the column following loading.

"Loading" as used herein, refers to the application of a sample to the column until the entire sample is contained within the column.

"Washing" as used herein, refers to the process of flowing solvent through the column after loading so as to remove substances not adsorbed on the column or substances from which the analyte is to be separated. Multiple washes are possible using different wash solutions.

"Sample" as used herein, refers to any solution comprising a mixture of large and small molecular weight species. Such samples include any type of biological samples such as body fluids or samples derived from cell culture, microorganisms, plants, or animals.

"Body fluid" as used herein means any fluid that can be isolated from the body of an individual. For example, "body fluid" may include blood, plasma, serum, bile, saliva, urine, tears, perspiration, synovial fluid, peritoneal fluid, bronchial-alveolar lavage, CSF, and the like.

"Small molecular weight species" or a "small molecule analyte" as used herein refers to a molecule that typically has a molecular weight of less than 5,000 daltons, more typically less than 1,000 daltons, and most typically less than 500 daltons. Following preparative isolation from the monolithic column, the analytes are then subjected to analytical chromatographic separation and detection.

"Large molecular weight species" as used herein refers to a molecule having a molecular weight in the range of one thousand to many millions of daltons. Examples include proteins, proteinaceous substances, nucleic acids, polysaccharides, and other polymers. "Proteinaceous substances" as used herein refer to any material that includes a polypeptide as part of the molecule. Proeteinaceous materials include glycoproteins, proteoglycans, lipoproteins, and the like. The term protein includes the terms "polypeptide," and "peptide," which refer to a polymer of amino acid residues. The term applies to amino acid polymers in which one or more amino acid residue is a synthetic chemical analogue (e.g., para-methyl-tyrosine, para-chloro-phenylanine, and the like) of a corresponding naturally occurring amino acid, as well as to naturally occurring amino acid polymers. Amino acids can be in the L or D form so long as the binding function of the peptide is maintained. Peptides can be of variable length, generally between about 4 and 200 amino acids. Peptides may be cyclic, having an intramolecular bond between two non-adjacent amino acids within the peptide, e.g., backbone to backbone, side-chain to backbone and side-chain to side-chain cyclization.

"In-line" as used herein refers to steps performed in sequence and in an automated fashion and without the need for operator intervention. For example, by careful selection of valves and connector plumbing, two or more chromatography columns can be connected as needed such that material is passed from one column to the next without the need for any manual handling steps. Alternatively, one column may be used in conjunction with one or more valves and connector plumbing so that the direction of the flow of mobile phase through the column may be reversed, allowing for an eluted analyte to be reapplied to the column. Such systems may require electronic programming of controlling software. In preferred embodiments, the selection of valves and plumbing is controlled by a computer pre-programmed to perform the necessary steps. In some embodiments, the chromatography system is connected in-line to a detector system, e.g., a mass spectrometry system.

"Off-line," in contrast, as used herein refers to a procedure requiring manual intervention of an operator. Thus, if samples are subjected to precipitation, and the supernatants are then manually loaded into an autosampler, the precipitation and loading steps are off-line from the subsequent steps.

"Eluent" as used herein refers generally to the liquid or gas entering a chromatographic bed (e.g., a column) used to effect a separation by "elution."

"Effluent" refers generally to a liquid that flows out of something. As used herein, "effluent" refers to the solvent flowing out of a column. Effluent may contain substances not retained on the columna or analytes eluted from the column.

"Reservoir" refers generally to a vessel or container entity for holding a liquid. As used herein "reservoir" may be used to hold the analyte after elution from the column. The analyte may be held in the reservoir until it is, for example, reloaded onto the column from which it was eluted, or directed to another column. Examples of reservoirs as used herein include a sample loop or tubing.

"Mobile phase source" as used herein refers to a vessel that holds mobile phase prior to its being utilized in a chromatographic separation.

"Hydrophobic" as used herein means not dissolving in water. "Hydrophobic" compounds include long straight or branched chain alkanes. A hydrophobic solvent is a solvent that is capable of dissolving a hydrophobic compound.

The choice of solvents or mobile phase used depend on the nature of the column used in a particular preparative or analytical separation. For example, solvents typically used with reversed phase columns typically include any miscible combination of water and various organic liquids (the most common are methanol or acetonitrile).

In certain embodiments, an analyte may be purified by applying a sample to a column under conditions where the analyte of interest is reversibly retained by the column, while one or more other materials are not retained. In these embodiments, a first mobile phase condition can be employed where the analyte of interest is retained by the column, and a second mobile phase condition can subsequently be employed to remove retained material from the column, once the non-retained materials are washed through. The second mobile phase may be phased in gradually to generate a concentration gradient, usually under computer control directing the composition of mobile phase over time, or by an immediate change in the mobile phase. In some embodiments, removal is accomplished with the use of a small volume of an organic solvent. The retained materials may also be removed from the column by "backflushing" the column, or reversing the direction of flow of the mobile phase. Such backflushing may be performed with the same mobile phase used in applying the analyte to the column or may be a different mobile phase for removing the retained material. This may be particularly convenient for material that is retained at the top of the column. Alternatively, an analyte may be purified by applying a sample to a column under mobile phase conditions where the analyte of interest elutes at a differential rate in comparison to one or more other materials.

BRIEF DESCRIPTION OF THE DRAWINGS

FIG. 1A shows the system in the first position. FIG. 1B shows the system in the second position.

FIG. 2A shows the valve in the first position and the direction of the solvent flow during column equilibration, sample loading, and detection of the eluted analyte. FIG. 2B shows the valve in the second position during the isolation of the retained analyte following the preparative chromatography.

FIG. 3A shows the first and second multiport valves both in the first position during column equilibration and sample loading. FIG. 3B shows the position of the first and second multiport valves (second position and first position, respectively) during the elution of analytes. FIG. 3C shows the position of the first and second multiport valves (first position and second position, respectively) during the elution and detection of the analyte.

DETAILED DESCRIPTION OF THE INVENTION

Figure 1A:
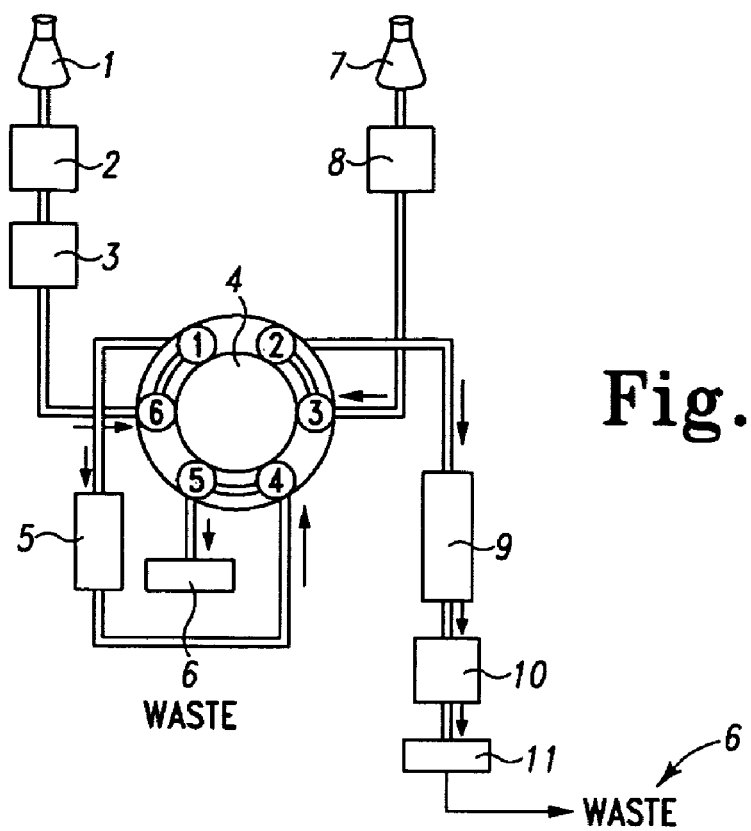
FIGS. 1A-B. Schematic of a two-column chromatography system comprising a monolithic preparative column and an analytical column.

In particular aspects, a preparative monolithic column is supplied in-line with an analytical column in a chromatography system. Such a system is set forth in FIG. 1A-B. Thus, referring to FIG. 1A, a first mobile phase source (1) is connected to a solvent delivery system (2) which is connected to a sample injector (3) which is connected to one port of a multiport valve (4). Other ports of the multiport valve (4) are connected to the top end of the preparative monolithic column (5), the bottom end of the preparative monolithic column (5), waste (6), the top end of the analytical column (9), and a second solvent delivery system (8), which is further connected to a second mobile phase source (7). The bottom end of the analytical column is further connected to a detector (10), which is connected to an optional data integrator (11).

Figure 1B:
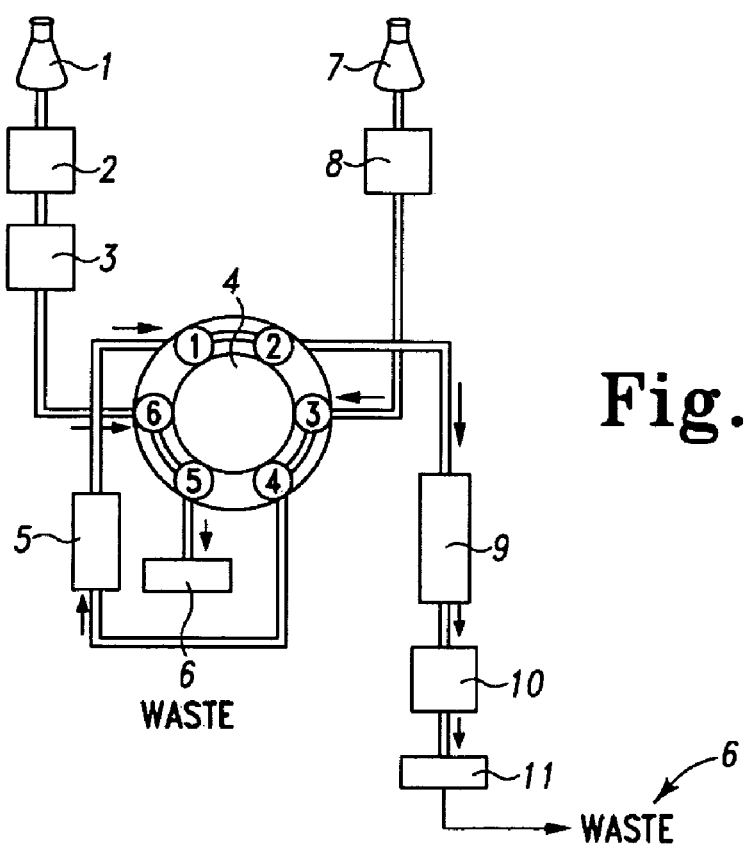

In the operation of the above system, mobile phase (1) is supplied to the system with a solvent delivery system (2). Samples are injected into the system downstream of the solvent delivery system with a sample injector (3) with the multiport valve (4) in the first position (FIG. 1A). The sample is transferred with mobile phase or buffer (1) using the solvent delivery system (2) onto the preparative column (5) containing a monolithic sorbent. The analytes of interest are selectively retained on the column (5) based on the size of the analyte, while the remaining biological materials (proteins etc.) are passed to the waste (6). After the multiport valve (4) has been switched to the second position (FIG. 1B), the analyte is eluted with the aid of an organic solvent (7) supplied by a second solvent delivery system (8), running in the reverse direction through preparative column (5) and supplied to the downstream analytical column (9). The analytical separation takes place under conditions sufficient to separate the analytes of interest. The eluted analytes are measured in the detector (10), and the data are evaluated in the integrator (11). The multiport valve is then switched to the first position so that the preparative column can be conditioned by means of the solvent delivery system (2) for a new preparative cycle.

Figure 2A:
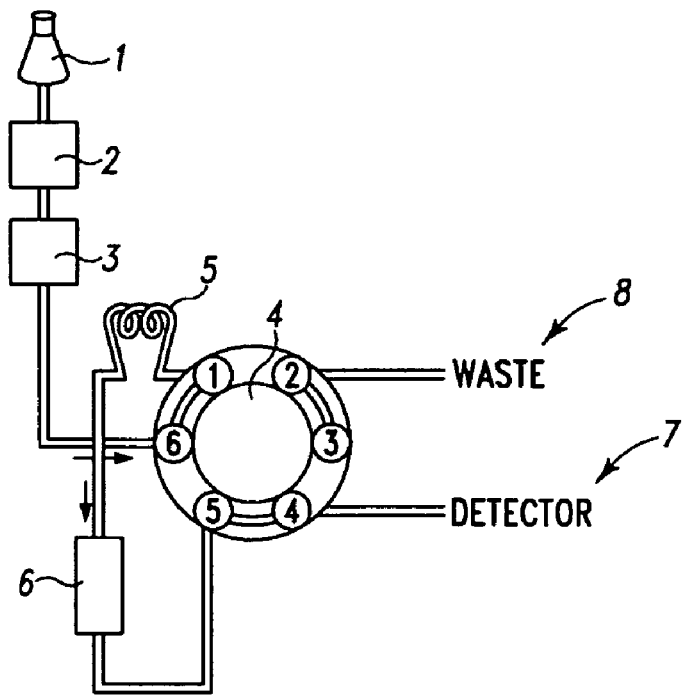
FIGS. 2A-B. Schematic of a single column chromatography system comprising a single monolithic column and one multiport valve, assembled so that the monolithic column may be used for both preparative and analytical chromatography.
Figure 2B:
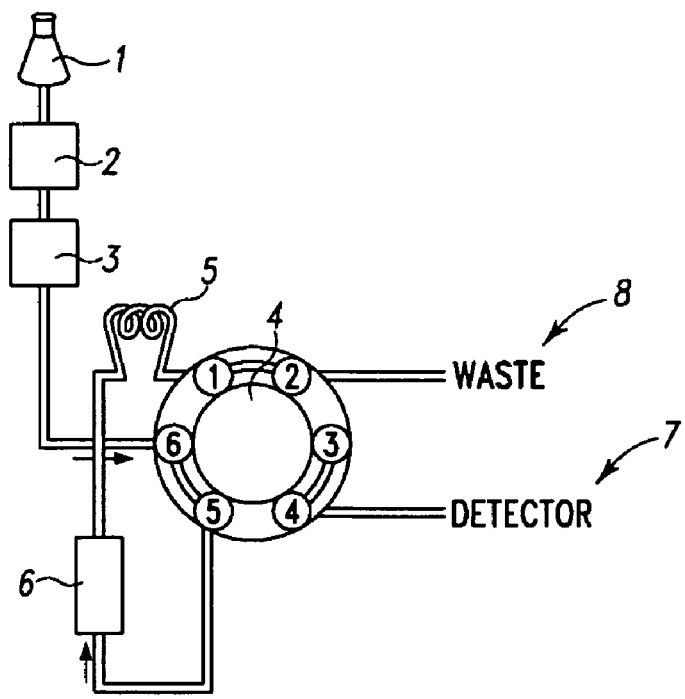

In other aspects, a single monolithic column is used in both preparative and analytical separations. There are at least two configurations of such a system. One example of such a system is set forth in FIG. 2A-B. Thus, referring to FIG. 2A, a mobile phase reservoir (1) is connected to a solvent delivery system (2) which is connected to a sample injector (3) which is connected to one port of a multiport valve (4). Other ports of the multiport valve (4) are connected to a reservoir (i.e., a sample loop) (5), the second opening of the column (6), a detector (7), and waste (8), which is connected to an optional data integrator (not shown). The sample loop connects to the first opening of the column (6).

During operation of the above system, mobile phase (1) is supplied to the system using a solvent delivery system (2). Sample is injected into the system with a sample injector (3), passed through the multiport valve (4) set in the first position, through the sample loop (5) and onto the monolithic column (6) under conditions such that the analyte of interest is retained on the column while large molecular weight species are swept off of the column and through the detector (see FIG. 2A). The valve (4) is then switched to the second position (see FIG. 2B), reversing the flow of mobile phase through the column, and the analyte is eluted from the column and into the sample loop (5). The valve (4) is switched back to the first position (see FIG. 2A) and the analyte is re-supplied to the column (6). The analyte may then be eluted off the column under conditions sufficient to separate the analyte or analytes of interest from each other or from other substances retained on the column and detected using the detector (7).

In a preferred embodiment of the above aspect of the invention, the system further comprises a second multiport valve, preferably connected in tandem with the first multiport valve. Such a system is set forth in FIG. 3A-C. Thus, referring to FIG. 3A, a first mobile phase source (1) is connected to a solvent delivery system (2), which is connected to a sample injector (3), which is connected to one port (shown as port #6) of a first multiport valve (4). Other ports of the multiport valve (4) are connected to a reservoir (i.e., sample loop) (5), the bottom end of the column (6), and a second multiport valve (7). The second valve (7) is further connected to waste (8) and a detector (9). The detector may be further connected to an optional data integrator (not shown).

Figure 3A:
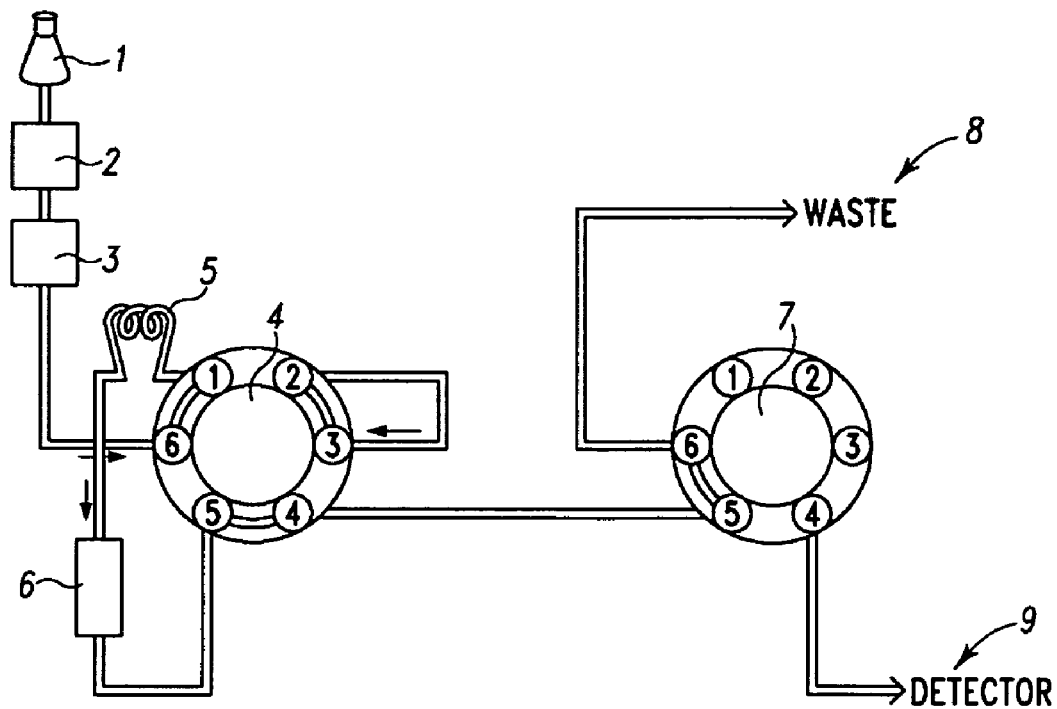
FIGS. 3A-C. Schematic of a single column chromatography system comprising a single monolithic column and two multiport valves (4) and (7) assembled so that the monolithic column may be used for both preparative and analytical chromatography.
Figure 3B:
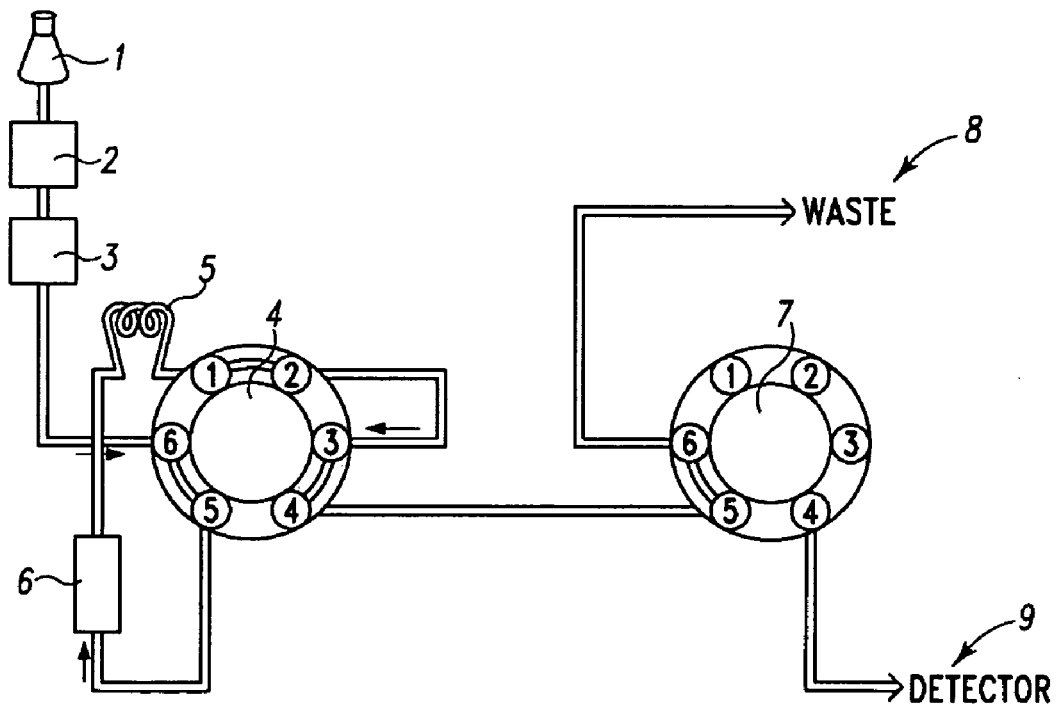
Figure 3C:
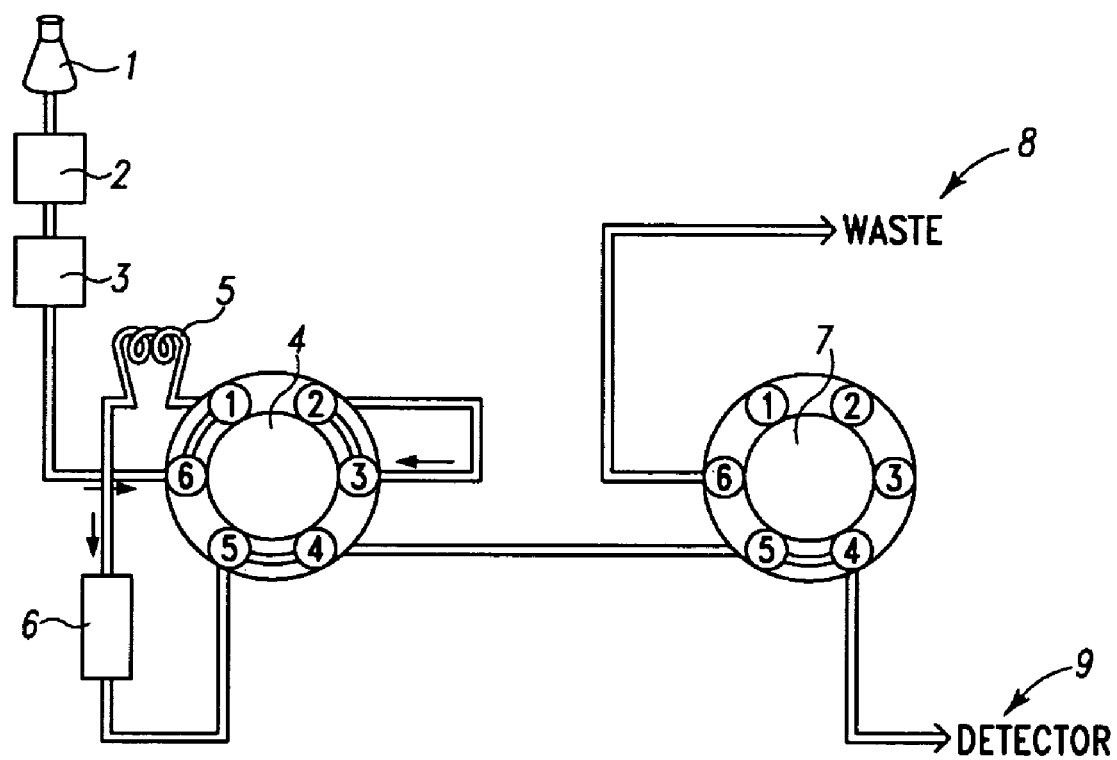

During the operation of the above system, mobile phase (1) is supplied to the system using solvent delivery system (2). Sample is injected into the system with a sample injector (3), passed through the first valve (4) set in first position through the sample loop (5) and onto the monolithic column (6) under conditions such that the analyte of interest is retained on the column while large molecular weight species are swept off of the column, through second valve (7) in the first position and into waste (8) (as shown in FIG. 3A). The first valve (4) is switched to the second position (as shown in FIG. 3B) and the analyte is eluted from the column and into the sample loop (5). The first valve (4) is then switched back to the first position (as shown in FIG. 3C) and the analyte is resupplied to the column (6). The second valve (7) is switched to the second position (as shown in FIG. 3C) so that flow of effluent will pass through the detector (9) (see FIG. 3C). The analyte is eluted off the column under conditions sufficient to separate the analyte or analytes of interest from each other or from other substances retained on the column.

Mobile Phase Supply

A mobile phase supply comprises a mobile phase source and a solvent delivery system. Such a solvent delivery system is a pumping device such as commercially available HPLC pumps, which provide solvent or mobile phase to a column. Such pumps generally provide pulse-free flows, flow rates ranging from 0.1-10 mL/min, accurate control of flow rate, generation of high pressure (up to 6000 psi), and corrosion- and solvent-resistant components. Reciprocating pumps consist of a small chamber into which the solvent is pumped by the back and forth motion of a motor-driven piston. Two check valves, which open and close alternately, control the direction and flow of solvent in and out of a cylinder. Single-piston pumps use specially designed cams to permit very rapid refill times, producing a more continuous flow. The disadvantage of pulsed flows with reciprocating pumps is often overcome by using a pulse damper. The use of a dual-piston pump, which operates with the pistons moving out of phase with each other, offers a reasonable solution for pulse-free fluid delivery.

A mobile phase "gradient" or "gradient elution" as used herein refers to steady changes in the mobile phase composition during a chromatographic run. The main purpose of gradient elution is to elute analytes that are strongly retained by the column faster, while having the weakly retained analytes eluted more slowly so that eluted analytes produce well resolved peaks upon detection. For example, in reversed phase chromatography, starting with a low content of the organic solvent in the eluent allows the weakly retained analytes to be separated. Strongly retained analytes will remain on the adsorbent surface at the top of the column, or will move very slowly. Increasing the amount of organic component in the eluent (e.g., acetonitrile) allows strongly retained components to move faster, because of the steady increase of the competition for the adsorption sites by the organic solvent.

Mobile phase gradients may be generated through high pressure mixing, which requires a pump for each solvent, or low pressure mixing which requires only one pump. In high-pressure mixing systems, individual high pressure pumps are used to provide each solvent. The outlet of each pump is either connected to a mixing connector (usually referred to as a "T" since there are normally two inlet lines and one outlet line) or to a mixing chamber. Thus, the two solvents are blended en route to the injector and column, that is, mixing is accomplished on the high-pressure side of the pumps. The generation of a mobile phase gradient created from three solvents may be accomplished by utilizing three separate pumps. In low-pressure systems, mixing is accomplished prior to the pump, at its low-pressure side and the overall flow rate is controlled by a single pump. Proportioning valves, normally solenoid operated, are used to deliver the individual solvents. The controller simply divides the signal according to the percentage of each component and each valve is opened for the proper period of time. Usually the valves deliver the individual solvents into a mixing chamber which then feeds the blended solvent to the pump. In some systems, the valves feed the mobile phase components through a mixing connector directly to the high-pressure pump. Programmable flow rate control is desirable for gradient generation by either method.

Sample Injector

A manual sample injector that is typically used comprises a 2-position valve that includes a fixed sample loop (e.g., 20 or 100 μl). In one configuration, the valve is set so that the flow from the pump is sent directly into the column; when the position of the valve is switched, the flow from the pump is diverted through the sample loop and into the column, thus supplying the sample to the column. Valves with electrically or pneumatically actuated position switches are commercially available and may be used.

Automated sample injectors (i.e., autosamplers) may be used in invention methods and systems. Such autosamplers can store and sequentially inject multiple samples are useful in high-throughput screening methods. Autosamplers are commercially available from a variety of sources.

Multiport Valve

Multiport valves or reversing valves are available in many configurations from many commercial sources. Such valves may have, for example, six, or, eight, or ten, or more ports and up to six positions. Such valves may be optionally controlled with an actuator, allowing for automated control of the position of the valve.

In one example, the multiport valve has 6 ports and two operating positions. Thus, the valve may be connected simultaneously to an injector (with a solvent delivery system connected upstream), the top end of a column, the bottom end of a column and a detector. The components may be configured so that the multiport valve, which has two operating positions, controls the direction of the flow of solvent through the column. In the first position, solvent flows from the solvent delivery system, through the sample injector, into the valve, through the sample loop and into the top of the column. The solvent then flows through the column, out of the bottom of the column and to the detector or waste line. In the second position, solvent flows through the solvent delivery system, into the valve, and into the bottom of the column. The solvent then flows in the opposite direction through the column, out of the top of the column and to the detector or waste line.

In another example, a second valve may be connected in tandem with the first valve. In this system, a solvent delivery system is connected to a sample injector which is connected one port of a multiport valve. The other ports of the multiport valve are connected to the top end of the column (via a sample loop) and the bottom end of the column, and to the second multiport valve. The second multiport valve is further connected to one or more detectors, or a detector and a waste line. The second valve, therefore, controls the flow of effluent from the column to either of one or more in-line detectors or waste. Thus, when the first valve is in the first position, the injector is connected to the valve which is connected to the sample loop which is connected to the top end of the column. The bottom end of the column is connected to the valve which is further connected to the second valve. The second valve has two operating positions so that when the second valve is in one position, the first valve is connected (via the second valve) to a detector or, when the valve is in the second position, to a waste line. An optional second detector may replace the waste line. In another example, a second chromatography column is connected to the second valve. In this system, the first valve is connected (via the second valve) to the second column (and to an optional downstream detector) or, when the valve is in the second position, to a waste line.

Columns

A monolithic column comprises a "monolith," a continuous bed consisting of a single piece of a highly porous solid material (see e.g., Tennikova T B, Svec F (1993) J Chromatogr 646:279). A distinguishing feature of this medium is that the mobile phase is forced to flow through the large pores of the medium. As a consequence, mass transport is enhanced by convection and has a positive effect on the separation. Monolithic supports commercially available include: silica gel based monolithic beds, polyacrylamide based monolithic beds, and rigid organic gel based monolithic beds.

Silica gel-based monolithic beds are solid rods of silica monolith that have been prepared according to a sol-gel process. This process is based on the hydrolysis and polycondensation of alkoxysilanes in the presence of water-soluble polymers. The method leads to "rods" made of a single piece of porous silica with a defined bimodal pore structure having macropores (of about 2 μm) and mesopores (of about 0.013 μm) when smaller rods intended for analytical purposes are prepared. These columns have about 80% porosity, which is 15% more than columns packed with standard particulate packing (see e.g., Nakanishi K, Soga N (1991) J Am Ceram Soc 74:2518; Cabrera K, Wieland G, Lubda D, Nakanishi K, Soga N, Minakuchi H, Unger K K (1998) Trends Anal Chem 17:50).

Polyacrylamide-based monolithic beds are made of swollen polyacrylamide gel compressed in the shape of columns. Such columns rely on the polymerization of monomers and in the chromatographic column. In the presence of salt, the polymer chains form aggregates into large bundles by hydrophobic interaction, creating voids between the bundles (irregularly shaped channels) large enough to permit a high hydrodynamic flow. Following polymerization, the bed is compressed by connecting it to an HPLC pump adjusted to a flow rate equal or higher than that used in subsequent runs. The resulting bed can be regarded as a rod or plug permeated by channels through which the eluent can pass upon application of pressure. The polymer chains form a dense, homogeneous network of nodules consisting of microparticles with an average diameter of 2 μm. The channels between the nodules are large enough to permit a high hydrodynamic flow (see e.g., Hjerten S, Liao J-L, Zhang R (1989) J Chromatogr 473:273; Liao J-L, Zhang R, Hjerten S (1991) J Chromatogr 586:21).

Rigid organic gel-based monolithic beds are prepared by free radical polymerization of a mixture of a polymerizable monomer, optionally with functional groups, such as glycidyl methacrylate, ethylene dimethacrylate, a crosslinking agent, a radical chain initiator, such as 2,2'-azobisisobutyronitrile, and porogenic solvents (cyclohexanol and dodecanol) in barrels of an appropriate mold in the case of glycidyl methacrylate-co-ethylene dimethacrylate (GMA-EDMA) monoliths (see e.g., Svec F, Tennikova T B (1991) J Bioact Compat Polym 6:393; Svec F, Jelinkova M, Votavova E (1991) Angew Macromol Chem 188:167; Svec F, Frechet J M J (1992) Anal Chem 64:820). Another method uses free radical polymerization of a mixture of styrene and divinylbenzene (as a crosslinking reagent) using 2,2'-azobisisobutyronitrile as an initiator and porogenic solvents (dodecanol and toluene) (Merhar M, J Liq Chromatogr 24:2429 (2001)). After polymerization, the formed block of polymer is washed, e.g. with methanol, followed by a methanol-water mixture (50:50) and distilled water to remove porogenes and residual monomers from the polymer. After this, the monolithic bed is ready for derivatization to achieve a desired chemistry or immobilization of ligands. GMA-EDMA monoliths have active epoxide groups which can easily be further modified using various chemicals, e.g. diethyl amine, propane sulfone for ion exchange chromatography, e.g. butyl groups for hydrophobic interaction chromatography and any desired protein ligand for affinity chromatography. Alternatively, the epoxide groups containing monolith material can be modified to obtain polar groups on the surface, e.g. by using acids, e.g. sulfuric acid; to obtain the monolith material in hydrolized form that carries OH groups. Depending on the adsorption and elution conditions, a monolith carrying polar groups, e.g. hydroxyl (OH) groups or amino ($NH_2$) groups, is suitable for being used in a variety of adsorption principles, e.g. the so-called "normal phase" chromatography (Dorsey J G, Foley J P, Cooper W T, Barford R A, Barth H G (1990) Anal. Chem. 62:324 R) or the so-called "hydrophilic interaction" chromatography (Alpert A J (1990) J. Chromatogr. 499:17), the so-called "cohydration/cosovent exclusion promoted chromatography" (Validated Biosystems: Purification Tools for Monoclonal Antibodies, Cagnon P (1996), 103) or the so-called "hydrogen bond chromatography" (Fujita T, Suzuki Y, Yamauti J, Takagahara I, Fujii K., Yamashita J, Horio T (1980) J. Biochem. (Tokyo), 87 (1):89).

A number of different columns are commercially available for use in analytical chromatography. These columns differ in the column packing material and thus, the means by which analytes are retained and include reversed-phase or hydrophobic interaction, ion exchange, size exclusion or gel permeation, and affinity columns. Numerous column packings are available for analytical chromatographic separation of samples, and selection of an appropriate separation protocol is an empirical process that depends on the sample characteristics, the analyte of interest, the interfering substances present and their characteristics, etc. For HPLC, polar, ion exchange (both cation and anion), hydrophobic interaction, phenyl, C-2, C-8, and C-18 columns are commercially available. During chromatography, the separation of materials is effected by variables such as choice of eluant (also known as a "mobile phase"), choice of gradient elution and the gradient conditions, temperature, etc.

In reversed phase (RP) liquid chromatography, the typical polar stationary phase is replaced with a hydrophobic stationary phase, thus the phase is "reversed." A reversed-phase column, then, retains hydrophobic analytes, which are eluted more readily as the proportion of the hydrophobic component of the mobile phase is increased. Exemplary columns include phenyl, C-2, C-4, C-8, and C-18.

Affinity chromatography is based on selective non-covalent interaction between an analyte and specific molecules. It is very specific, but not very robust. It is often used in biochemistry in the purification of proteins protein constructs (e.g., fusion proteins, tagged proteins, and the like).

Detection and Identification of Analyte

In some embodiments, a mass spectrometer is used in-line for detection and identification of the analyte.

The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000), each of which is hereby incorporated by reference in its entirety, including all tables, figures, and claims.

For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

Moreover, one can often enhance the resolution of the MS technique by employing "tandem mass spectrometry," or "MS/MS." In this technique, a first, or parent, ion generated from a molecule of interest can be filtered in an MS instrument, and these parent ions subsequently fragmented to yield one or more second, or daughter, ions that are then analyzed in a second MS procedure. By careful selection of parent ions, only ions produced by certain analytes are passed to the fragmentation chamber, where collision with atoms of an inert gas to produce these daughter ions. Because both the parent and daughter ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps can be combined in methods known as "MS/MS$^n$." Various other combinations may be employed, such as MS/MS/TOF, MALDI/MS/MS/TOF, or SELDI/MS/MS/TOF mass spectrometry.

Ions can be produced using a variety of methods including, but not limited to, electron ionization, chemical ionization, fast atom bombardment, field desorption, and matrix-assisted laser desorption ionization ("MALDI"), surface enhanced laser desorption ionization ("SELDI"), photon ionization, electrospray ionization, and inductively coupled plasma.

The term "electron ionization" as used herein refers to methods in which an analyte of interest in a gaseous or vapor phase is interacted with a flow of electrons. Impact of the electrons with the analyte produces analyte ions, which may then be subjected to a mass spectroscopy technique.

The term "chemical ionization" as used herein refers to methods in which a reagent gas (e.g. ammonia) is subjected to electron impact, and analyte ions are formed by the interaction of reagent gas ions and analyte molecules.

The term "fast atom bombardment" as used herein refers to methods in which a beam of high energy atoms (often Xe or Ar) impacts a non-volatile test sample, desorbing and ionizing molecules contained in the sample. Samples are dissolved in a viscous liquid matrix, such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

The term "field desorption" as used herein refers to methods in which a non-volatile test sample is placed on an ionization surface, and an intense electric field is used to generate analyte ions.

The term "matrix-assisted laser desorption ionization," or "MALDI" as used herein refers to methods in which a non-volatile sample is exposed to laser irradiation, which desorbs and ionizes analytes in the sample by various ionization pathways, including photo-onization, protonation, deprotonation, and cluster decay. For MALDI, the sample is mixed with an energy-absorbing matrix, which facilitates desorption of analyte molecules.

The term "surface enhanced laser desorption ionization," or "SELDI" as used herein refers to another method in which a non-volatile sample is exposd to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization" or ESI as used herein refers to methods in which a solution is passed along a short length of capillary tube, to the end of which is applied a high positive or negative electric potential. Solution reaching the end of the tube, is vaporized (nebulized) into a Jet or spray of very small droplets of solution in solvent vapor. This mist of droplets flows through an evaporation chamber which is heated slightly to prevent condensation and to evaporate solvent. As the droplets get smaller the electrical surface charge density increases until such time that the natural repulsion between like charges causes ions as well as neutral molecules to be released.

The term "Atmospheric Pressure Chemical Ionization," or "APCI," as used herein refers to methods that are similar to ESI; however, APCI produces ions by ion-molecule reactions that occur within aplasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated N2 gas may be used to improve removal of solvent. The gas-phase ionization in APCI can be more effective than ESI for analyzing less-polar species.

The term "inductively coupled plasma" as used herein refers to methods in which a sample is interacted with a partially ionized gas at a sufficiently high temperature to atomize and ionize most elements.

The term "ionization" as used herein refers to the process of generating an analyte ion having a net electrical charge equal to one or more electron units. Negative ions are those ions having a net negative charge of one or more electron units, while positive ions are those ions having a net positive charge of one or more electron units.

The term "operating in negative ion mode" refers to those mass spectrometry methods where negative ions are detected. Similarly, "operating in positive ion mode" refers to those mass spectrometry methods where positive ions are detected.

The term "desorption" as used herein refers to the removal of an analyte from a surface and/or the entry of an analyte into a gaseous phase.

In those embodiments, such as MS/MS, where parent ions are isolated for further fragmentation, collision-induced dissociation, or "CID," is often used to generate the ion fragments for further detection. In CID, parent ions gain energy through collisions with an inert gas, and subsequently fragment by a process referred to as "unimolecular decomposition." Sufficient energy must be deposited in the parent ion so that certain bonds within the ion can be broken due to increased vibrational energy.

In other embodiments, any of a variety of standard HPLC detectors can be used for the detection of the analyte upon elution from the analytical column. In this case, the elution of a compound from the column is detected as a peak in a chromatogram. The retention time of the peak is used to identify the compound, and the peak height (or area) is proportional to the amount of the compound in the sample. The "retention time" is the time required for an analyte to pass through a chromatographic system and is measured from the time of injection to the time of detection. Ideally, each analyte of interest will have a characteristic retention time. However, the retention of an analyte often differs considerably between experiments and laboratories due to variations of the eluent, the stationary phase, temperature, and the setup of the chromatographic system. Therefore the retention time of the test analyte is compared to that of one or more standard compounds under identical conditions. An appropriate detector exhibits good sensitivity, good stability, reproducibility, linear response over a few orders of magnitude, short response time, and ease of operation. Such detectors include, but are not limited to, UV/Vis absorbance detectors, photodiodearray detectors, fluorescence detectors, refractive index detectors, and conductivity detectors.

UV/Vis absorbance detectors consisting of a scanning spectrophotometer with grating optics can be used. The independent or combined use of a Deuterium source (UV range, 190-360 nm) with a Tungsten source (visible range, 360-800 nm) provides a simple means of detecting absorbing species as they emerge from the column.

Photodiode-array (PDA)-based instruments are UV/Vis absorbance detectors that permit very rapid collection of data over a selected spectral range. Absorbance spectral data for each chromatographic peak can be collected and stored. Stored data may be compared with the spectrum of a pure standard from a library. The PDA detector is useful in the identification of components that are difficult to resolve (overlapping peaks) since the characteristic spectrum for each of the unresolved components is likely to be different.

Fluorescence detectors are useful in the detection of analytes that exhibit a chemiluminescent property such as fluorescence or phosphorescence. They are more sensitive than UV absorbance detectors by at least one order of magnitude. Fluorescence is typically observed by detection of the grating-isolated emission radiation at a 90-degree angle to the excitation beam. The number of fluorescing species can be enhanced by a post-column derivatization (PCD) reaction of the eluted compounds (or pre-column derivatization reaction of the sample itself) with special reagents.

Refractive index (RI) detectors respond to nearly all solutes. The difference in the refractive index of the reference mobile phase versus the column effluent results in the detection of separated components as peaks on the chromatogram. Because of its extreme sensitivity to the mobile phase, this detector may not be used without adequate pulse-damping within the LC pump, nor is it suitable for gradient applications because of the changing mobile phase composition. The detection limits are usually lower than those observed with absorbance detectors.

Conductivity detectors provide high-sensitivity detection of all charged species. This detector may be used with an HPLC system for the simple and reliable quantification of anions, cations, metals, organic acids, and surfactants down to the ppb level. The addition of a chemical suppressor between the column and conductivity detector serves to reduce the eluant conductivity, allowing the use of gradient elution and the determination of ppb levels with minimum baseline drift. For a typical determination of low levels of anions, the eluant is converted to its weakly ionized low-conductivity acid (e.g., $Na_2CO_3$ to carbonic acid), reducing the background noise. At the same time, the analyte anions are converted to their corresponding high-conductivity acids (e.g., NaCl to HCl), increasing the relative analyte signal.

Data Collection

A record of the detector response may be obtained using a chart recorder or an integrator. Automated data and method storage, data processing, and reporting can be performed with standard PC-based data collection packages.

Example 1

A sample of serum was assayed for estradiol using a monolithic column for preparative chromatography followed by in-line analytical chromatography using a second column.

Figure 7A:
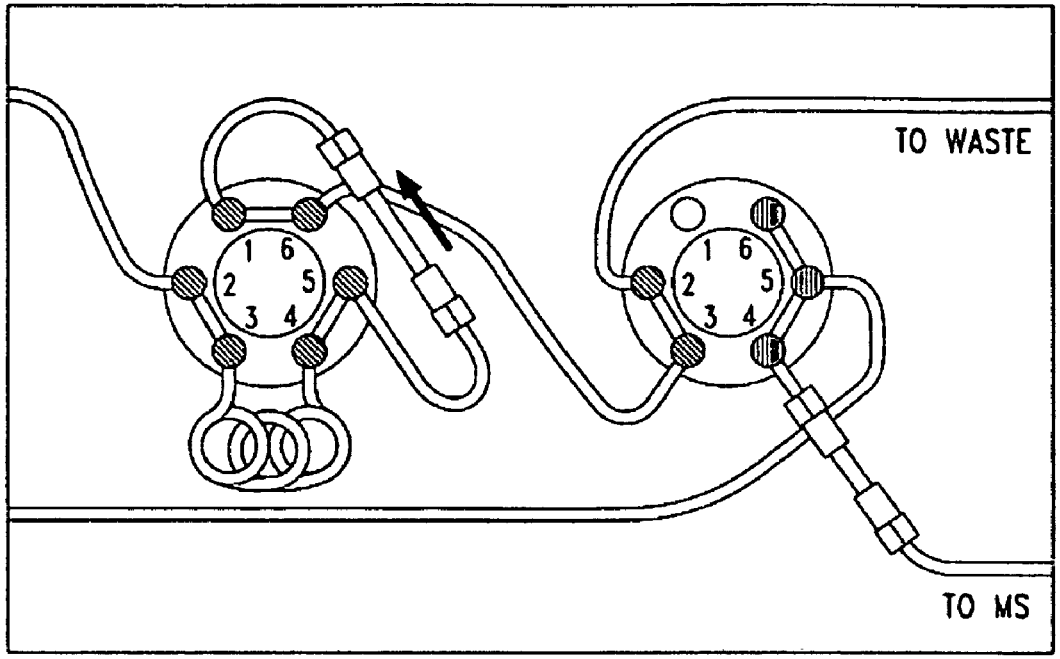
FIG. 7A-C Schematic of the HTLC system used in the analysis of estradiol in a sample of serum using a monolithic column for preparative chromatography followed by in-line analytical chromatography using a second column, as described in Example 1.

An HTLC system was used which comprised two LC pumps (quaternary pump or binary), two multiport valves, a monolithic C18 column (50×4.6 mm, mesopore 130 Å, macropore 2 μm, porosity >80%), an ether-linked phenyl phase column (100×2.0 mm, 80 Å, 4 μm), a 100 μL sample loop, and a mass spectrometer ("ms"). The system was configured as shown in FIG. 7A-C.

The first pump was connected to port 2 of the first multiport valve, the 100 μL sample loop was connected to ports 3 and 4, and the first column (the monolithic C18 column) was located between ports 1 and 5. The second multiport valve was connected, via port 3, to the first multiport valve at port 6. The second valve was further connected to the second column (the ether-linked phenyl phase column), which was further connected to a mass spectrometer ("MS") via port 4, and a waste line via port 2.

Figure 6:
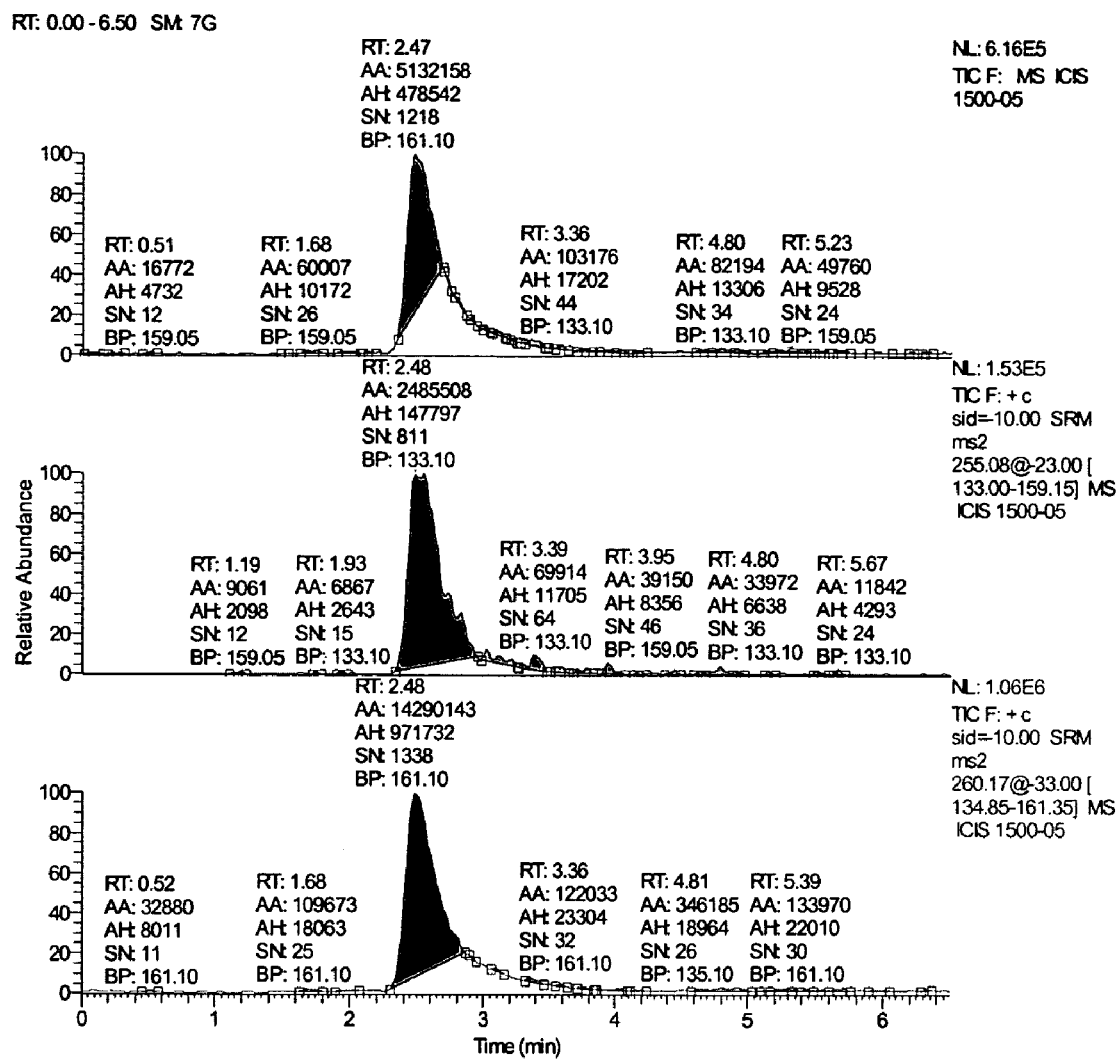
FIG. 6. Chromatograms showing the separation of estradiol and D8-estradiol internal standard in a serum sample from the large molecule background, produced with the use of a monolithic column for both preparative chromatography and analytical chromatography.

The solvents used were as follows:
Solvent A: 0.1% formic acid
Solvent B: 100% methanol The samples were processed by adding 200 μL of serum and diluting with 300 μL of 20% formic acid in water and adding 25 μL of the internal standard in methanol. The columns were equilibrated with both multiport valves in the "LOAD" position (see FIG. 7A) using 100% solvent A from the first pump. 80 μL of the processed sample was injected onto the column using 100% solvent A at a flow rate of 4-5 mL/min for 30 seconds. The first multiport valve was switched to the "ELUTE" position (see FIG. 7B) and the column was backflushed with 100% solvent B from the first pump at a flow rate of 1 mL/min for 60 seconds to elute retained analytes from the column into the 200 μL sample loop. The second multiport valve was switched to the "ELUTE" position (see FIG. 7C) and the eluted analytes were applied to the second column using 95% solvent A:5% solvent B from the first pump at a flow rate of 1 mL/min for 15 seconds. The second multiport valve was switched to the "LOAD" position (see FIG. 7B) and the analytes were eluted with a gradient of 95% solvent A: 5% solvent B to 100% solvent B generated by the second pump and run at a flow rate of 1.6 mL/min over 200 seconds. Eluted analytes were detected using the in-line mass spectrometer. A peak corresponding to a retention time of 2.48 minutes was observed and determined to be estradiol. D8-estradiol, run as an internal standard, exhibited a retention time of 2.48 minutes. The resulting chromatograms are shown in FIG. 6.

Figure 7B:
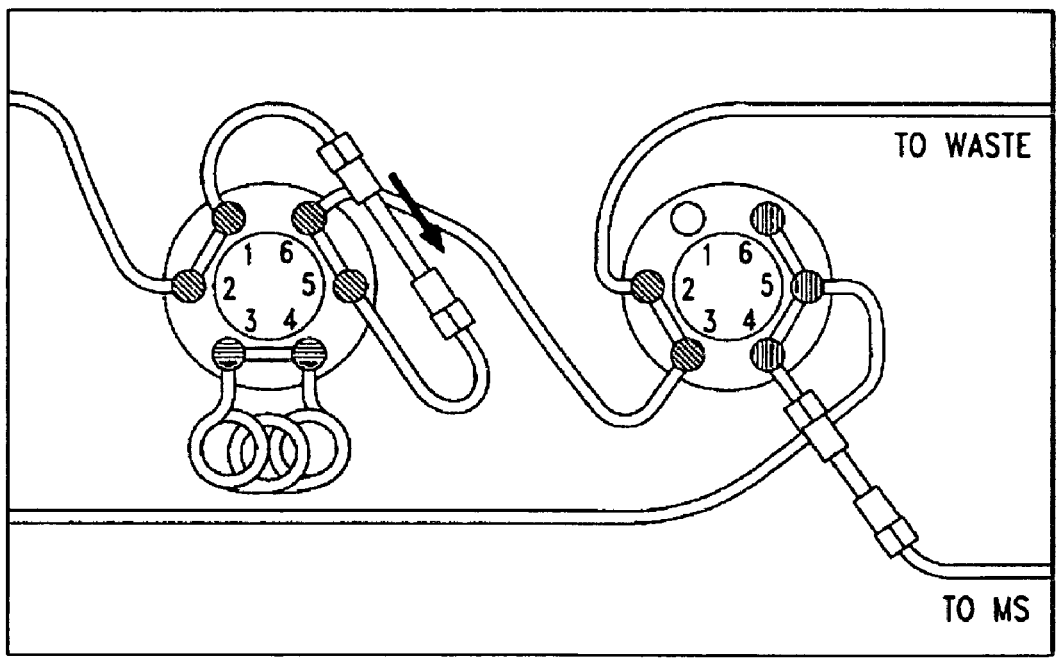
Figure 7C:
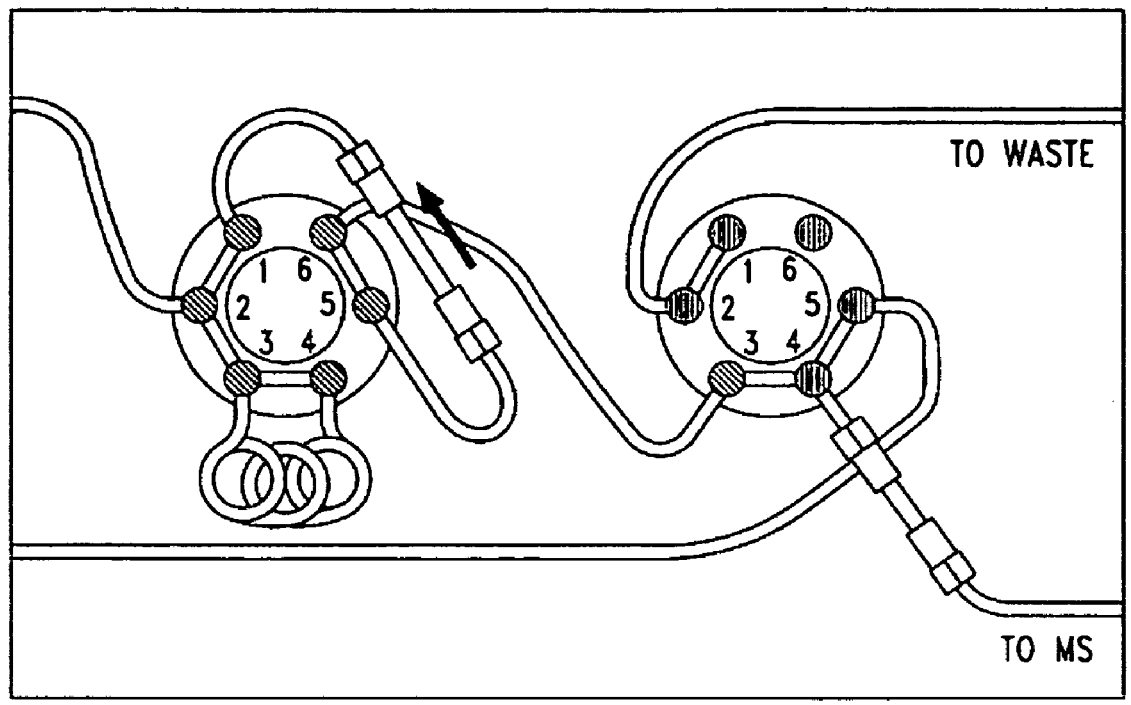

To recharge the column for subsequent samples, the first column was backflushed with 100% solvent B from the first pump at a flow rate of 4-5 mL/min for 60 seconds with the first multiport valve in the "ELUTE" position and the second multiport valve in the "LOAD" position (see FIG. 7B). The first multiport valve was switched to the "LOAD" position (see FIG. 7A) and the column was equilibrated with 100% solvent A from the first pump at a flow rate of 5 mL/min for 40 seconds.

Example 2

A sample of serum was assayed for estradiol using a single monolithic column for both preparative chromatography and analytical chromatography.

Figure 4A:
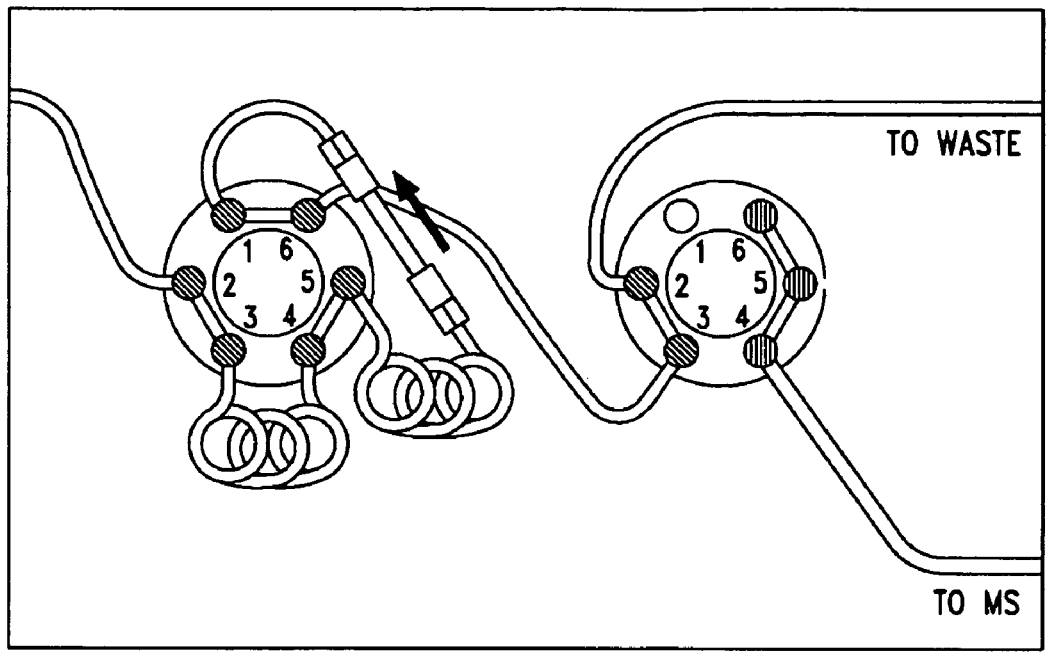
FIG. 4A-C. Schematic of the HTLC system used in the analysis of estradiol in a sample of serum using a single monolithic column for extraction and analysis, as described in Example 2.
Figure 4B:
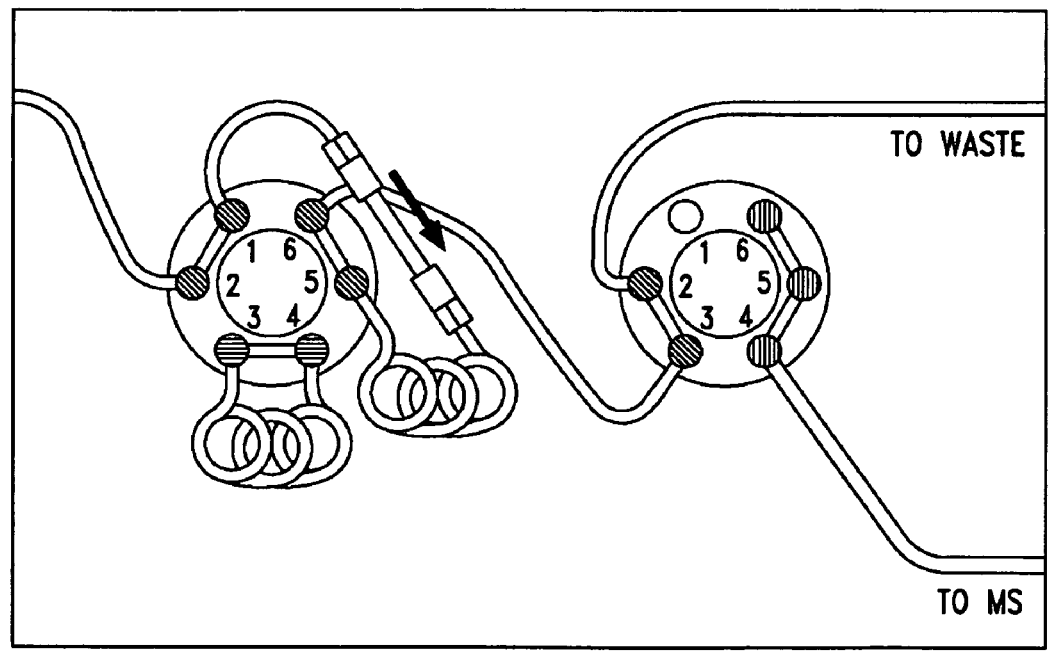
Figure 4C:
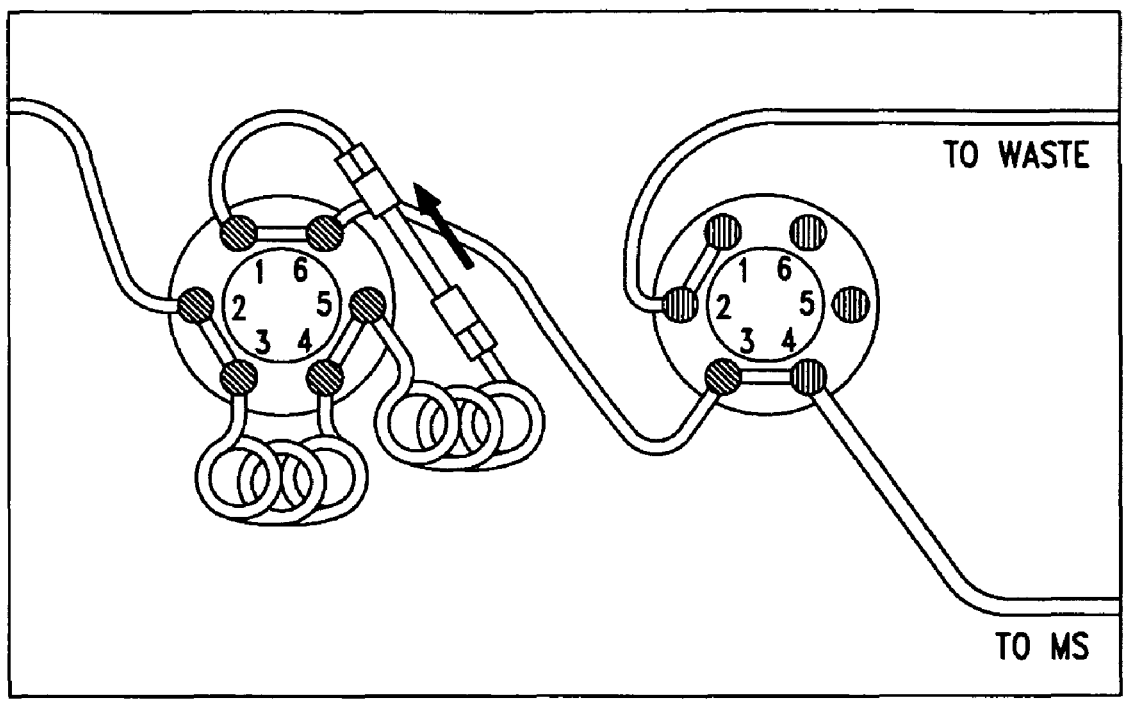
Figure 5:
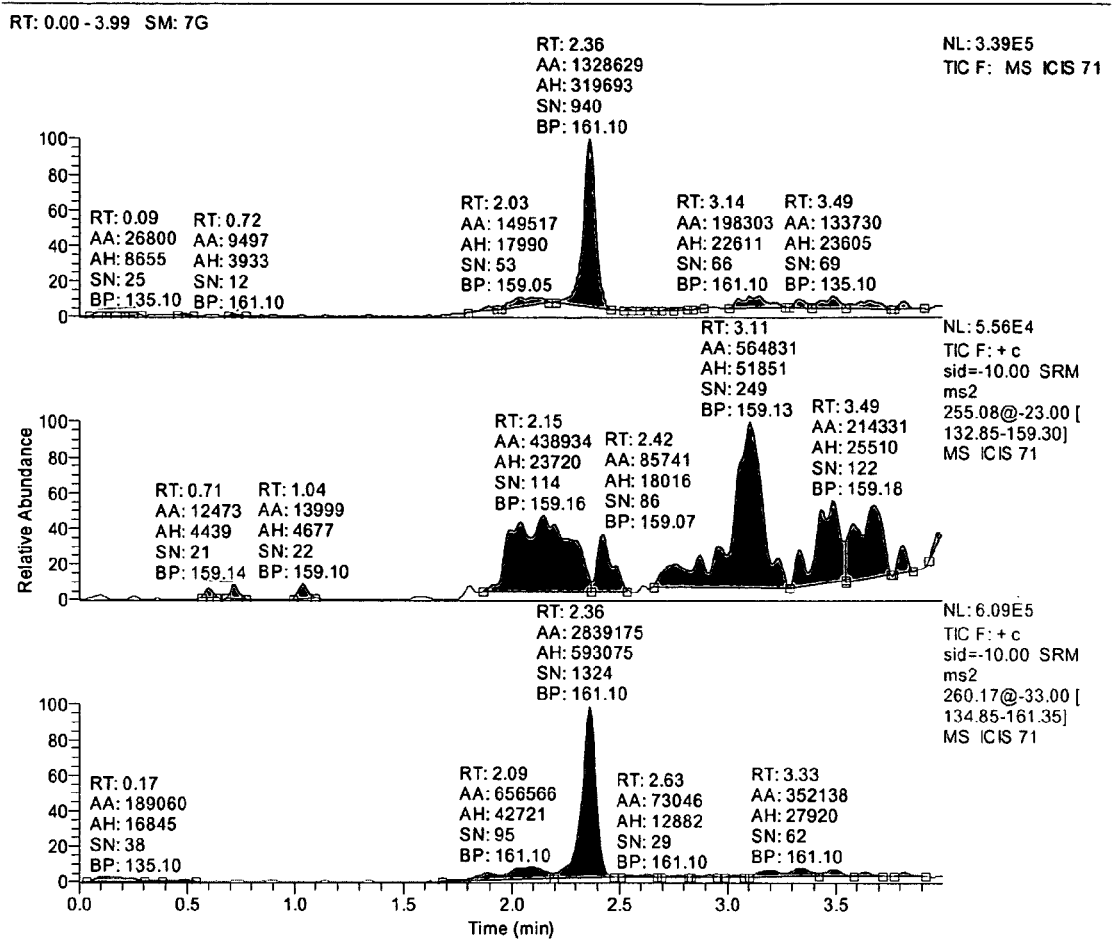
FIG. 5. Chromatograms showing the separation of estradiol and D8-estradiol internal standard in a serum sample from the large molecule background, produced with the use of a monolithic column for preparative chromatography in-line with analytical HPLC.

An HTLC system was used which comprised a quaternary pump, two multiport valves, a monolithic C18 column (50×4.6 mm, mesopore 130 Å, macropore 2 μm, porosity >80%), a 100 L sample loop, a 200 μL sample loop, and a mass spectrometer. The system was connected as in FIG. 4A-C. The quaternary pump (not shown) was connected to port 2 of the first multiport valve, the 100 μL sample loop was connected to ports 3 and 4, and the 200 μL sample loop was connected between port 5 and the column. The second multiport valve was connected, via port 3, to the first multiport valve at port 6. The second valve was further connected to a mass spectrometer ("MS") via port 4 and a waste line via port 2.

The solvents used were as follows:
Solvent A: 0.1% formic acid
Solvent B: 100% methanol A sample of serum was diluted in solvent A. The column was equilibrated with both multiport valves in the "LOAD" position (see FIG. 4A) using 100% solvent A. 50 μL of the diluted sample was injected onto the column using 100% solvent A at a flow rate of 5 mL/min for 35 seconds. The first multiport valve was switched to the "ELUTE" position (see FIG. 4B) and the column was backflushed with 100% solvent B at a flow rate of 1 mL/min for 60 seconds to elute retained analytes from the column and into the 200 μL sample loop. The first multiport valve was switched to the "LOAD" position and the second multiport valve was switched to the "ELUTE" position (see FIG. 4C) and the eluted analytes were reapplied to the column using 95% solvent A:5% solvent B at a flow rate of 1 mL/min for 15 seconds. The analytes were eluted with a gradient of 95% solvent A:5% solvent B to 100% solvent B at a flow rate of 1.6 mL/min over 200 seconds and detected using the in-line mass spectrometer. A peak corresponding to a retention time of 2.48 minutes was observed and determined to be estradiol. D8-estradiol was run as a separate sample for use as an internal standard and exhibited a retention time of 2.48 minutes. The resulting chromatograms are shown in FIG. 6.

To recharge the column for subsequent samples, the first multiport valve was switched to the "ELUTE" and the second multiport valve switched to the "LOAD" position and the column was backflushed with 100% solvent B at a flow rate of 5 mL/min for 60 seconds. The first multiport valve was switched to the "LOAD" position and the column was equilibrated with 100% solvent A at a flow rate of 5 mL/min for 40 seconds.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A chromatographic method for detecting one or more analytes in a body fluid sample containing a mixture of other substances, said method comprising:
    a) separating said one or more analytes from said other, substances in a mixture using a first chromatography column comprising a monolithic sorbent having macropores and mesopores, using a first mobile phase under conditions such that said one or more analytes are retained on said first column and other substances are removed; wherein said one or more analytes retained on said first column have a molecular weight of less than about 5,000 daltons,
    b) eluting said one or more retained analytes by applying a second mobile phase to the column,
    c) directing the eluted one or more analytes to a second chromatography column in-line with said first column for further separation, and
    d) detecting said one or more analytes following the separation in step c).

2. A method according to claim 1, wherein said second mobile phase is applied to the column in the opposite direction of the flow in step a).

3. A method according to claim 1, wherein said body fluid is selected from the group consisting of blood, plasma, serum, bile, saliva, urine, tears, synovial fluid, peritoneal fluid, bronchial-alveolar lavage, CSF, and perspiration.

4. A method according to claim 1 wherein said macropores have a median diameter of 0.1 to 50 µm.

5. A method according to claim 4 wherein said macropores have a median diameter of 2 to 20 µm.

6. A method according to claim 1 wherein said mesopores have a median diameter of 2 to 100 nm.

7. A method according to claim 1, wherein said mesopores comprise a fatty acid linked to said mesopore.

8. A method according to claim 7, wherein said fatty acid is selected from the group consisting of butyric acid (C4), caprylic acid (C8), and stearic acid (C18).

9. A method according to claim 1, wherein said one or more analytes retained on said first column have a molecular weight of less than about 1,000 daltons.

10. A method according to claim 1, wherein said one or more analytes retained on said first column have a molecular weight of less than about 500 daltons.

11. A method according to claim 1, wherein said other substances are proteins or proteinaceous material.

* * * * *